United States Patent [19]
Manabe

[11] Patent Number: 4,613,122
[45] Date of Patent: Sep. 23, 1986

[54] CT COUCH APPARATUS HAVING A LIFT

[75] Inventor: Yoshinori Manabe, Ootawara, Japan

[73] Assignee: Kabushiki Kaisha Toshiba, Kawasaki, Japan

[21] Appl. No.: 641,575

[22] Filed: Aug. 16, 1984

[30] Foreign Application Priority Data

Aug. 19, 1983 [JP] Japan ................................. 58-150191

[51] Int. Cl.$^4$ ............................................... A61B 6/02
[52] U.S. Cl. .................................... 269/322; 254/122;
378/209
[58] Field of Search ............... 269/322; 254/9 C, 122,
254/124; 187/18; 378/208–209; 108/90, 97, 28;
5/503, 508

[56] References Cited

U.S. PATENT DOCUMENTS 3,623,707 11/1971 Klopp .................................... 254/122
4,131,802 12/1978 Braden et al. ......................... 378/208
4,506,872 3/1985 Westerbery et al. ................. 378/209

Primary Examiner—Robert C. Watson
Attorney, Agent, or Firm—Finnegan, Henderson, Farabow, Garrett & Dunner

[57] ABSTRACT

First and second arms are supported, rotatable to each other and in the shape of X, by a shaft. The lower end of the first arm is on the side of a scan gantry and rotatably supported on a base by means of a rotation fulcrum. The lower end of the second arm and upper ends of the first and second arms are supported by base and frame rails through movement fulcrums to be rotatable in relation to and movable along the rails. A tension spring is stretched between the second arm and a mounting frame to urge the mounting frame toward the scan gantry. Stoppers are arranged in the frame rails to prevent the movement fulcrums of the first and second arms from moving from their predetermined positions in the direction of their separating from the scan gantry. The first arms are rotated and erected by a hydraulic cylinder. The mounting frame is lifted along an arc whose center is the rotation fulcrum, with the first arms contacting the first stoppers, and then vertically lifted, with the second arms contacting the second stoppers.

12 Claims, 7 Drawing Figures

CT COUCH APPARATUS HAVING A LIFT

BACKGROUND OF THE INVENTION

The present invention relates to a CT couch apparatus having a lift employed by the radiation computed tomography apparatus and serving to move up and down the table top of the couch on which the patient lies so as to place the patient inside the opening of the scan gantry and pull him back from the opening.

In order to obtain tomographic images of the patient with the radiation CT apparatus or X-ray CT apparatus, for example, it is necessary that the patient is located exactly at the predetermined position inside the opening of the scan gantry.

FIG. 1 shows the conventional CT couch, located behind a scan gantry 10 when viewed in a direction shown by an arrow 4, and a mounting frame 16, supported on a base 14 by means of a pair of parallel arms 20 and 22. The arms 20 and 22 are not moved relative to each other but rotatably connected to the base 14 and mounting frame 16. A patient couch 18 can be shifted longitudinally in relation to its mounting frame 16.

The arms 20 and 22 are sloped to the greatest extent thereof and a patient 2 is laid down on the couch 18 in this condition. The arms 20 and 22 are then rotated and erected by means of a hydraulic pump (not shown) to lift the mounting frame 16. When the patient 2 is lifted to the predetermined position behind an opening 12 of the scan gantry 10, the lifting of the mounting frame 16 is stopped. Linear crossing light beams 24 are projected toward the patient 2 at this predetermined position, and the position of the couch 18 is adjusted to accord the ear hole of the patient 2 with the crossing point of the crossing light beams 24. The couch 18 is then shifted relative to the mounting frame 16 and that part of the patient 2 which is to be scanned with X-rays is located at a tomographic image position 26 inside the opening 12.

When the patient 2 at the predetermined position is lower than an area 28 inside the scan gantry 10 where tomographic images of the patient 2 are obtained, it is necessary that the arms 20 and 22 are further rotated to make the position of the mounting frame 16 higher. However, the mounting frame 16 is moved forward in the direction 4 by the rotation of the arms 20 and 22. For the purpose aligning the ear hole of the patient 2 with the crossing point of the crossing light beam 24, therefore, it is necessary that the couch 18 be moved backward in relation to the mounting frame 16 when viewed in the direction 4. Several processes are necessary to position the patient, thereby making the operation complicated. In addition, an AC motor is usually used to move the couch 18, but it is likely to move the couch 18 beyond a predetermined position, thereby making it difficult to exactly locate the couch 18. A DC motor may be used to avoid this, but a DC motor is expensive.

Since the arms 20 and 22 are parallel to each other, they have a limited sloping angle, thereby making it difficult to locate the couch 18 at a low position.

SUMMARY OF THE INVENTION

The object of the present invention is to provide a CT couch apparatus having a lift capable of moving a mounting frame not in the horizontal but vertical direction and easily and quickly locating a patient at a predetermined position.

A CT couch apparatus having a lift for placing a patient inside the opening of a scan gantry according to the present invention comprises a base provided with a pair of parallel base rails; a couch on which the patient is laid down; a mounting frame for supporting the couch to advance and retreat the latter into and from the opening of the scan gantry and having a pair of frame rails parallel to the base rails; an arm structure arranged on the base to support the mounting frame and including arm assemblies each of which comprises a pair of first and second arms attached to the base and frame rails, respectively, a shaft for supporting the arms of the arm assembly, rotatable to each other, in the shape of an X, a rotating fulcrum for supporting the lower end of the first arm, rotatable relative to the base, and for moving the fulcrums for supporting the lower end of the second arm and upper ends of the both arms, rotatable in relation to and movable along the base and frame rails; a means for rotating the arms in the direction of erecting them relative to the base; an elastic means for urging the mounting frame in a first direction along the frame rails and in relation to the base; and first and second stoppers for preventing the moving fulcrums at the upper ends of the first and second arms from moving, relative to the mounting frame, in a direction reverse to the first direction. The first stopper is contacted with the moving fulcrum of the first arm by the elastic member when the mounting frame is located between a position where the patient is placed on and off the couch and a shifted position which is higher than the patient-placing position. The second stopper is contacted with the moving fulcrum of the second arm by the elastic member when the mounting frame is located between the shifted position and a position where the couch is inserted into the opening of the scan gantry.

When the arms are rotated and erected by the rotating means, the mounting frame lifts along a track which takes the rotating fulcrum as its center, keeping the moving fulcrum of the upper end of the first arm in contact with the first stopper by means of the elastic means. When the moving fulcrum at the upper end of the second arm is then in contact with the second stopper, the first stopper is separated from the moving fulcrum and the mounting frame lifts vertically upward, keeping the moving fulcrum of the second arm in contact with the second stopper. The mounting frame in the scan gantry moves not in the horizontal but vertical direction. Therefore, the mounting frame does not move in the horizontal direction, as it did in the conventional case, at the time of exactly adjusting the height of the mounting frame, so that the exact adjustment of height of the mounting frame can be achieved once and thereby enabling the patient to be easily and quickly located at the predetermined position.

DETAILED DESCRIPTION OF THE PREFERRED EMBODIMENT

Figure 2:
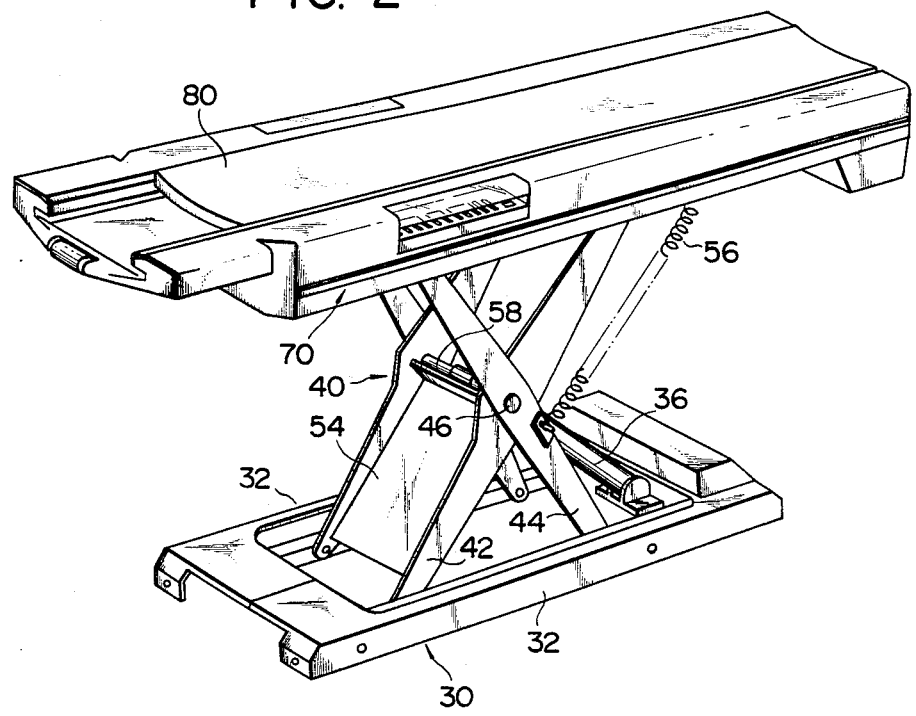
FIG. 2 is a perspective view showing an example of the CT couch apparatus having a lift according to the present invention.
Figure 3:
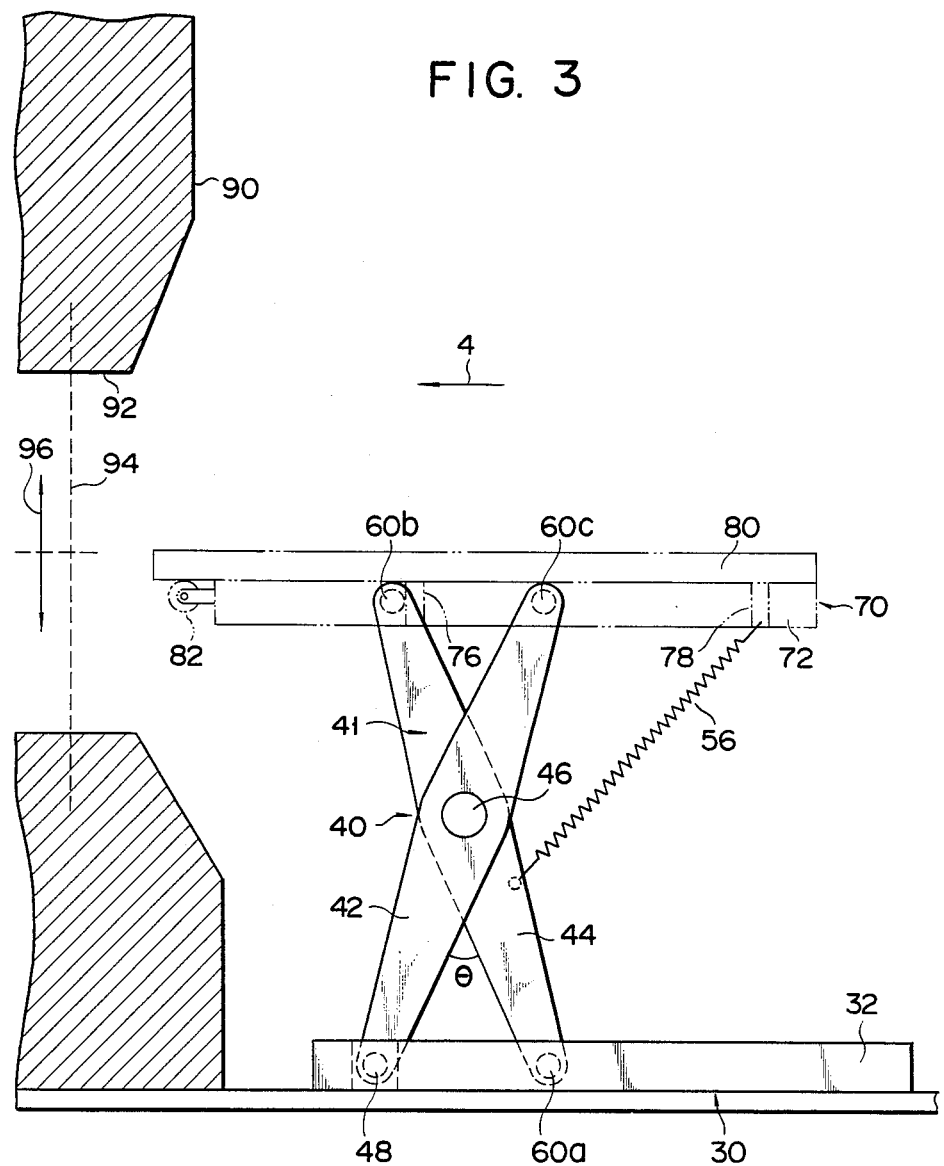
FIGS. 3 through 5 show the operation of the CT couch shown in FIG. 2.

FIGS. 2 and 3 show a CT couch apparatus having a lift embodied according to the present invention. This lift is located behind a scan gantry 90 when viewed in a direction shown by an arrow 4. An arm structure 40 is arranged on a base 30. A mounting frame 70 for supporting a couch 80 is supported by the arm structure 40, which is an X-shape when viewed from the front thereof and which has a pair of arm assemblies 41 separated from each other in the width direction of the base 30. Each of the arm assemblies 41 has a pair of arms 42, 44 rotatably connected to each other by a shaft 46. Fixed to the pair of arms 42 is a connector plate 54, by which the pair of arms 42 are separated from each other in the length direction of the shaft 46 and held parallel to each other. In each of the arm assemblies 41, therefore, the arms 42 and 44 can change their crossing angle, keeping them X-shaped while the respective arms 42 or 44 are parallel to each other (see FIGS. 3 through 5). Arranged at the lower end of the arm 42 of each arm assembly 41 is a rotation fulcrum 48 such as the bearing to rotatably support the arm 42 at the front end portion of the base 30 when viewed in the direction 4. A movement fulcrum 60a is arranged at the lower end of each of the arms 44. The base 30 has a pair of parallel rails 32 extending in the direction 4 thereon. The movement fulcrums 60a are engaged with the rails 32 and can move along the rails 32, changing the slope of the arms 44. A hydraulic cylinder 36 is arranged on the base 30, and its piston rod (not shown) is rotatably connected to a connector shaft 58 arranged between the pair of parallel arms 42. The arms 42 are continuously erected as the piston rod advances.

Movement fulcrums 60b and 60c are arranged at the upper ends of the arms 42 and 44. The mounting frame 70 has a pair of parallel rails 72 extending in the direction 4. The movement fulcrums 60b and 60c are engaged with the rails 72, respectively, and can move along the rails 72, changing the slope of the arms 42 and 44.

Figure 6:
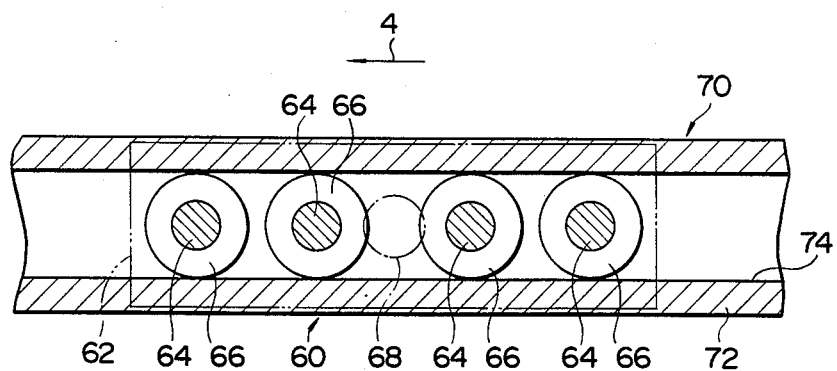
FIG. 6 shows a connector mechanism between an arm and a mounting frame.
Figure 7:
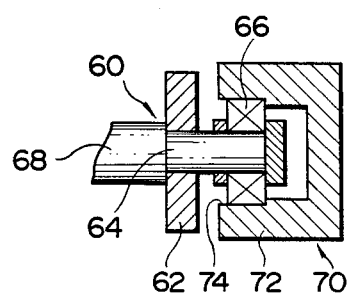
FIG. 7 is a traverse-sectioned view showing this connector mechanism.

Each of these movement fulcrums 60a, 60b and 60c have the same structure, which will be described next referring to FIGS. 6 and 7. The movement fulcrum 60 (60a, 60b, 60c) has a support plate 62 which extends along the rail 72. Four rods 64, separated from one another in the direction 4, are attached to the support plate 62, and a roller 66 is rotatably attached to each rod 64 by means of a bearing or the like. The four rollers 66 are engaged with a recess 74 of the rail 72. Two of the rods 64 are forced upward to urge their corresponding two rollers 66 against the upper edge of the recess 74, while the remaining two rods 64 are forced downward to urge their corresponding two rollers 66 against the lower edge of the recess 74. These four rollers 66, which are urged upward and downward, enable the support plate 62 to smoothly move in relation to the rail 72. A connector shaft 68 is fixed to the support plate 62. This connector shaft 68 is rotatably connected to the end of the arm 42 or 44. Since the movement fulcrum 60 is arranged as described above, the ends of the arms 42 and 44 can move along the rails 32 or 72, changing their slope relative to the rails.

A tension spring 56 is stretched between a position at the back end of the mounting frame 70 when viewed in the direction 4 and a position at the arm 44 which is lower than the shaft 46. The arms 42 and 44 are urged by this spring 56 in such a way that the angle $\theta$ which is formed between the arms 42 and 44 below the shaft 46 increases. The mounting frame 70 is also urged forward in the direction 4 by the spring 56.

A first stopper 76 is located at the front of the rail 72 of the mounting frame 70 and a second stopper 78 at the back thereof when viewed in the direction 4. The first stopper 76 prevents the movement fulcrum 60b from moving beyond the first stopper 76 backward in the direction 4, while the second stopper 78 prevents the movement fulcrum 60c from moving beyond the second stopper 78 backward in the direction 4.

The couch 80 is mounted on the mounting frame 70 to shift in the longitudinal direction of the frame 70. A roller 82 which is rotatably in contact with the underside of the couch 80 is attached to that end face of the mounting frame 70 located on the side of the scan gantry 90. When the couch 80 is advanced to the side of the scan gantry 90, it is supported by this roller 82. The couch 80 is reciprocated in the direction 4 by a driver means (not shown) on the mounting frame 70. The driver means may comprise an endless chain extending along the mounting frame, sprockets between which the chain is stretched, and a motor which drives the sprockets through gears, for example.

Figure 5:
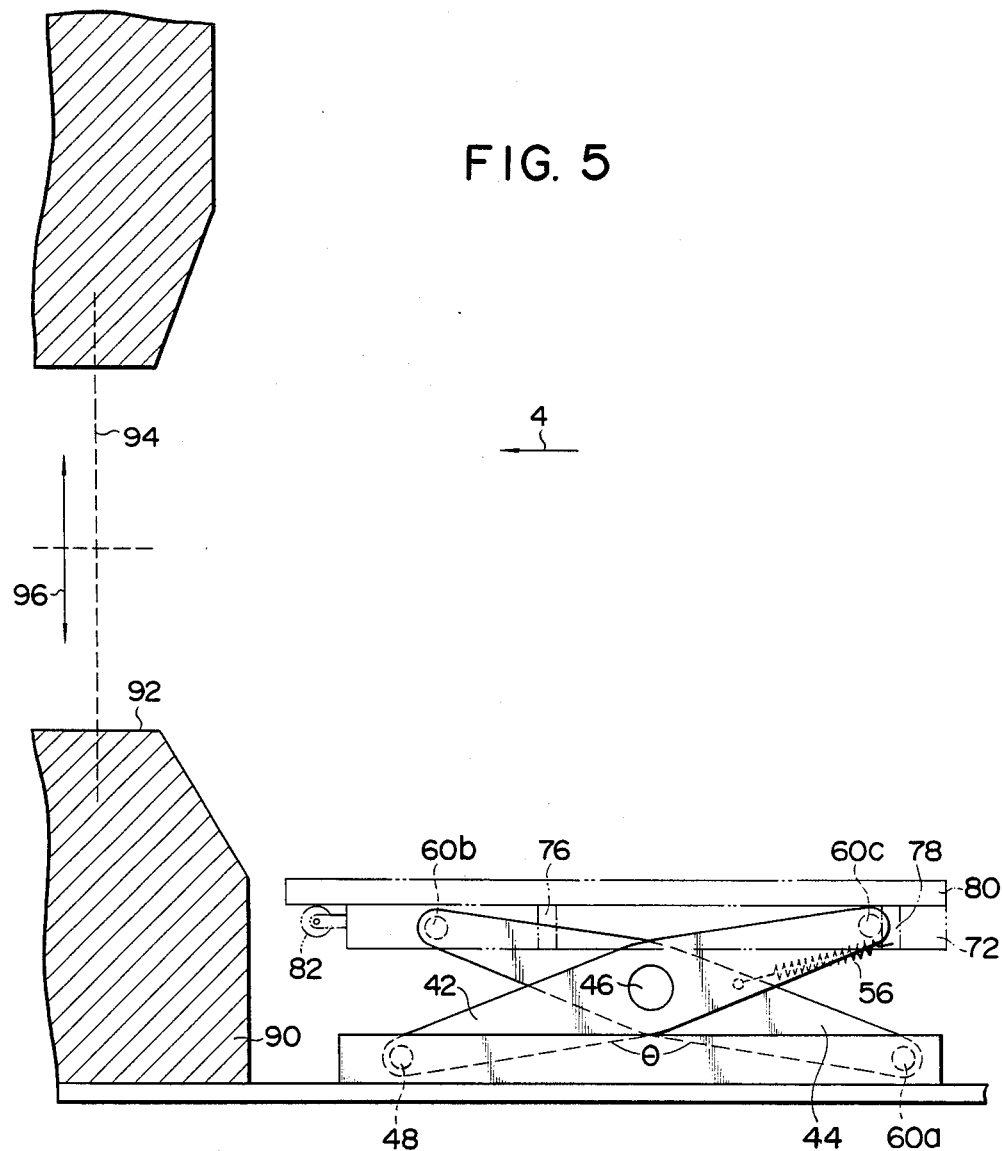

The hydraulic cylinder 36 is left inoperative, and the arms 42 and 44 of the arm structure 40 are held to make the largest angle $\theta$, as shown in FIG. 5. The mounting frame 70 is in its lowest position in this state. The mounting frame 70 is pulled by the spring 54, thereby causing the movement fulcrum 60c to strike against the stopper 78. The patient is placed on the couch 80 in this state. The hydraulic cylinder 36 is then operated to rotate the arms 42 in the direction in which they are erected. The angle $\theta$ thus decreases and the mounting frame 70 is lifted horizontally. Since the movement fulcrum 60c is in contact with the stopper 78 in this case, it is moved along an arc whose center is the rotation fulcrum 48.

Figure 4:
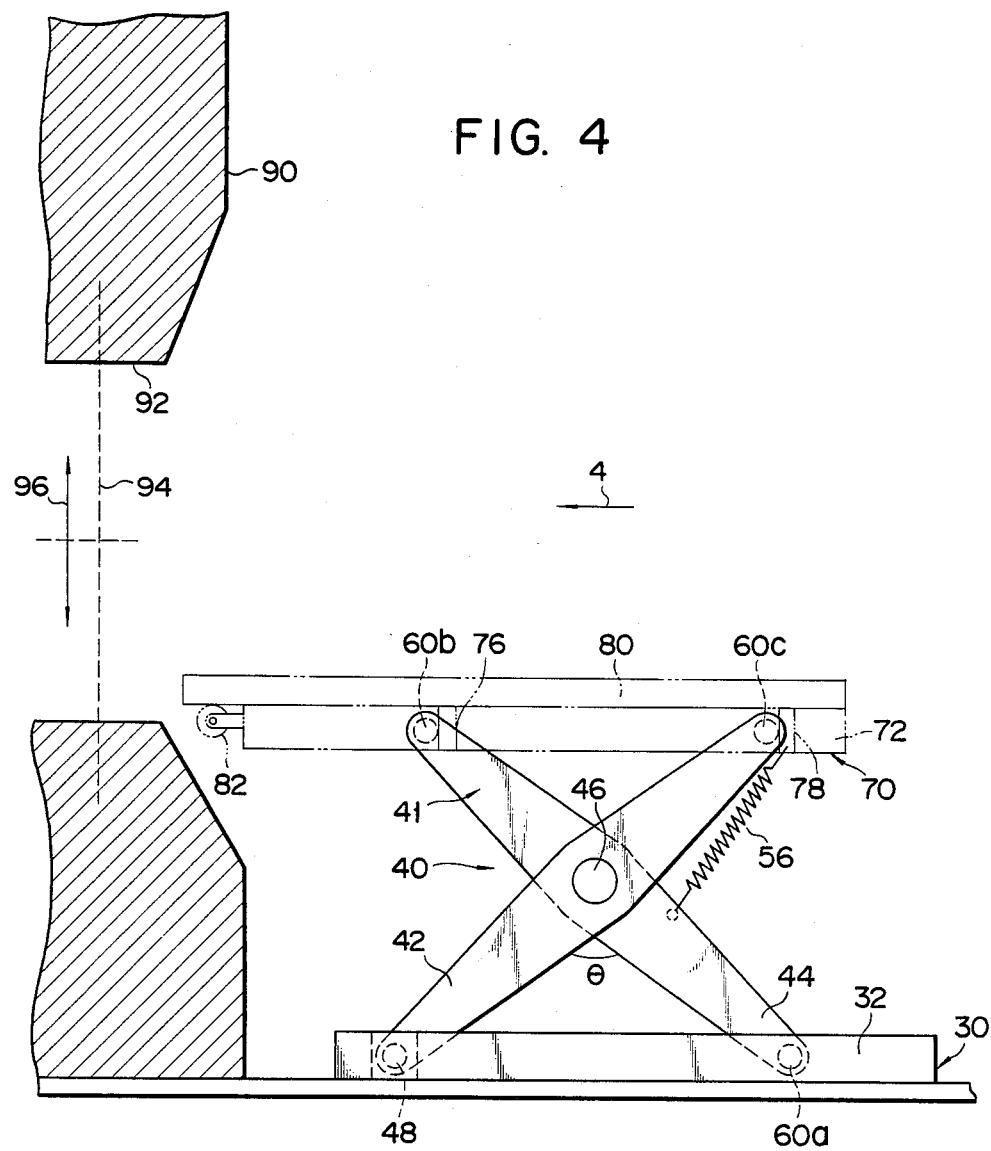

The movement fulcrum 60b moves along the rail 72 toward the stopper 76, as shown in FIG. 4, and finally strikes against the stopper 76. When the hydraulic cylinder 36 rotates the arms 42 and 44 to further lift them, the movement fulcrum 60c is moved to separate from the stopper 78, leaving the movement fulcrum 60b in contact with the stopper 76, as shown in FIG. 3. More specifically, when the hydraulic cylinder 36 lifts the arms 42 and 44 from their position shown in FIG. 4 to their position shown in FIG. 3, the mounting frame 70 is not moved in the direction 4 because the movement fulcrum 60b is contacted with the stopper 76, but the movement fulcrum 60c is moved in the direction 4 against the spring 56. When the movement fulcrum 60b is in contact with the stopper 76 (or the mounting frame is lifted from its position shown in FIG. 4 to its position shown in FIG. 3), the mounting frame 70 is moved not in the direction 4 but in the upward or vertical direction.

When the mounting frame 70 is lifted like this to a predetermined position, as shown in FIG. 3, the hydraulic cylinder is stopped. The driver means is operated to shift the couch 80 relative to the mounting frame 70 in the direction 4 and locate the patient on the couch 80 at a photographing position 94 in an opening 92 of the scan gantry 90. This photographing position 94 is irradiated by linear cross lights which cross each other and the patient is positioned using these cross lights. When the position of the patient is lower than the center of a photographing area 96 where sectional images of the patient's body tissues can be photographed, the hydraulic cylinder 36 is again operated to rotate the arms 42 and 44 slightly in the direction of further reducing the angle θ, thereby lifting the mounting frame 70. Since the stopper 76 contacts the movement fulcrum 60b at this time of finely adjusting the height of the mounting frame 70, the mounting frame 70 is moved not in the direction 4 but only in the upward or vertical direction. It is therefore unnecessary to conventionally rotate the arms 42 and 44 and move the couch 80, but the height adjustment of the mounting frame 70 can be finished with one adjustment. When the mounting frame 70 is lifted till the patient's ear hole is aligned with the crossing point of the cross lights, for example, the hydraulic cylinder 36 is stopped. A predetermined number of sectional images are photographed, moving the couch 80 in relation to the mounting frame 70. The couch 80 is pulled back from the opening 92 after the photographing operation, and the pressure of the hydraulic cylinder 36 is removed. The mounting frame 70 is thus lowered, retracing the track made when lifted, due to the tension force of the spring 54 as well as the weight of the couch 80, mounting frame 70 and patient. In short, the mounting frame 70 carries out only the lowering movement under the state that the movement fulcrum 60b is contacted with the stopper 76 (FIGS. 3 and 4). The mounting frame 70 is then lowered while returning backward in the direction 4 along the arc whose center is the rotation fulcrum 48, under the state that the movement fulcrum 60c contacts the stopper 78.

Figure 1:
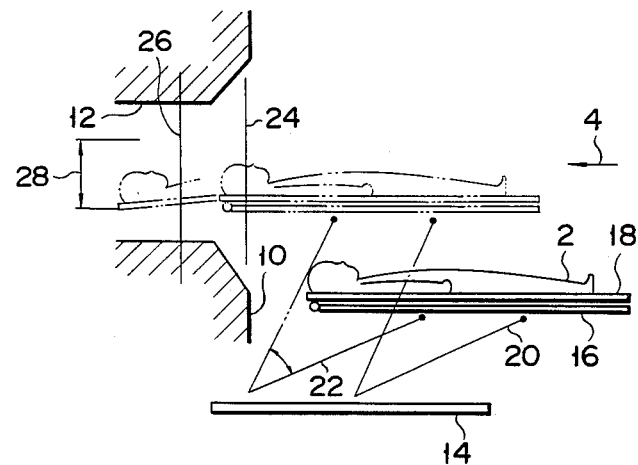
FIG. 1 shows the conventional CT couch.

As described above, the positioning of the patient can be easily and quickly achieved by slightly adjusting the height of the mounting frame 70. It should be understood that the present invention is not limited to the above-described embodiment but various changes and modifications can be made. Although the cross lights for positioning the patient have been employed at the photographing position 94 in the case of the above-described embodiment, the position of the cross lights may be on this side of the photographing position (see FIG. 1). There is only one spring 56 in the above-described embodiment. However, the action of urging the arms 42 and 44 to reduce the angle θ may be achieved by a spring, and the action of urging the mounting frame toward the scan gantry 90 may be attained by another spring. More specifically, a spring for urging the X-shaped arms 42 and 44 to reduce the angle θ may be arranged between the arms 42 and 44 left or right of the shaft 46, while another tension spring for urging the mounting frame 70 forward in the direction 4 may be arranged between the mounting frame 70 and the arm 42 adjacent to its movement fulcrum 60c. The elastic means need not be limited to a spring.

What is claimed is:

1. A CT couch apparatus for lifting a patient from an initial patient-placing position, through an intermediate position, to a final position aligned with the opening of a scan gantry comprising:
   a base having at least one base rail;
   a couch on which the patient is to be laid;
   a mounting frame for slidably supporting said couch so it can advance into and retreat from the opening of the scan gantry, said mounting frame having at least one frame rail;
   an arm structure for supporting said mounting frame relative to said base, said arm structure including at least a first arm and a second arm, said arms being pivotally fixed to each other at their mid portions to form the shape of an X;
   first, second and third movement fulcrums;
   said first arm being pivotally fixed at its lower end to said base and being pivotally fixed at its upper end to the first movement fulcrum, said first movement fulcrum being slidable along said frame rail;
   said second arm being pivotally fixed at its upper end to the second movement fulcrum and being pivotally fixed at its lower end to the third movement fulcrum, said second movement fulcrum being slidable along said frame rail and said third movement fulcrum being slidable along said base rail;
   means for pivoting said arms in the direction that lifts their upper ends and said mounting frame relative to said base;
   first stopper means for preventing the first movement fulcrum from sliding along said frame rail in a first direction beyond a preselected position;
   second stopper means for preventing the second movement fulcrum from sliding along said base rail in the first direction beyond a preselected position;
   a resilient means for urging said first movement fulcrum toward engagement with said first stopper means; and
   said first and second stopper means being positioned so that the first stopper means contacts said first movement fulcrum when the mounting frame is located between the patient-placing position and the intermediate position and the second stopper means contacts the second movement fulcrum when the mounting frame is located between the intermediate position and the final position.

2. The CT couch apparatus of claim 1 wherein said base rail and said frame rail are both substantially horizontal.

3. The CT couch apparatus of claim 1 further comprising means for urging said arms to pivot in the direction that lowers their upper ends and the mounting frame relative to the base.

4. The CT couch apparatus of claim 1 wherein said base has a pair of parallel, substantially horizontal base rails, said mounting frame has a pair of parallel, substantially horizontal frame rails, and said arm structure includes a pair of parallel first arms and a pair of parallel second arms.

5. The CT couch apparatus of claim 4 further comprising a connector member for holding said pair of first arms to each other.

6. The CT couch apparatus of claim 1 wherein said first arm is pivotally fixed to said base at a point nearer the scan gantry than the third movement fulcrum and wherein the first direction is away from the scan gantry.

7. The CT couch apparatus of claim 1 wherein said means for pivoting includes a member attached to said first arm for rotating said first arm about its lower end.

8. The CT couch apparatus of claim 7 wherein said resilient means includes a tension spring fixed at one end to the mounting frame and fixed at the other end to the second arm.

9. The CT couch apparatus of claim 1 wherein said rotating means includes a hydraulic cylinder with a piston rod, said hydraulic cylinder being mounted on said base and said piston rod being connected to said first arm at a position above its lower end whereby the first arm is rotated and erected by the advancement of the piston rod.

10. The CT couch apparatus of claim 1 wherein each of said movement fulcrums includes a support plate rotatably attached to the respective arm and extended along the longitudinal direction of the respective rail, plural roller rods separated from one another in the longitudinal direction of the respective rail and attached to the support plate, and rollers rotatably attached to the roller rods and engaged with the respective rail.

11. The CT couch apparatus of claim 1 wherein each frame and base rail has a U-shaped section and the respective movement fulcrum for sliding along a rail includes four rollers fitted between the edges of the rail, two of the rollers being urged against one edge of the rail and the other two rollers being urged against the other edge of the rail.

12. The CT couch apparatus of claim 1 further comprising means for advancing and retreating said couch.

* * * * *